(12) United States Patent
Hsieh

(10) Patent No.: US 6,327,325 B1
(45) Date of Patent: Dec. 4, 2001

(54) METHODS AND APPARATUS FOR ADAPTIVE INTERPOLATION REDUCED VIEW CT SCAN

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/504,834

(22) Filed: Feb. 16, 2000

(51) Int. Cl.$^7$ .......................................................... A61B 6/03
(52) U.S. Cl. ................................................. 378/4; 378/901
(58) Field of Search .................... 378/4, 19, 901

(56) References Cited

U.S. PATENT DOCUMENTS

| 5,828,718 | * | 10/1998 | Ruth et al. | 378/19 |
| 5,848,117 | * | 12/1998 | Urchuk et al. | 378/19 |
| 5,907,593 | * | 5/1999 | Hsieh et al. | 378/4 |

OTHER PUBLICATIONS

Hsieh, U.S. Pat. App. 09/440,733, filed Nov. 16, 1999 (copy not attached).

* cited by examiner

Primary Examiner—David V. Bruce
(74) Attorney, Agent, or Firm—Armstrong Teasdale LLP; Christian G Cabou

(57) ABSTRACT

One aspect of the present invention is a method for computerized tomographic (CT) imaging of an object. One embodiment of the method includes scanning an object with a CT imaging system to acquire views that include projection samples of an object; interpolating the acquired views within a selected view range to produce interpolated views; weighting the interpolated views to compensate for the interpolation; weighting the acquired views; and filtering and backprojecting the weighted, interpolated views and the weighted acquired views to generate an image of the object. View aliasing artifacts are reduced by this embodiment without using conjugate samples.

22 Claims, 1 Drawing Sheet

METHODS AND APPARATUS FOR ADAPTIVE INTERPOLATION REDUCED VIEW CT SCAN

BACKGROUND OF THE INVENTION

This invention relates to tomographic imaging, and more particularly to methods and apparatus for reducing aliasing artifacts in computerized tomographic imaging.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT imaging system is available that combines a gantry rotation rate of 0.8 s with a data acquisition system (DAS) sampling rate of 1230 Hz. As a result, a projection sampling rate of 984 views per gantry rotation. Theoretical, experimental, and clinical investigations have shown that, from a standpoint of aliasing, this sampling rate is near a lower limit. It would be desirable to increase the scan rate to at least 0.5 s per gantry rotation to reduce motion artifacts and to reduce imaging times, but to do so would require a higher sampling rate. Hardware limitations limit maximum sampling rates, however. For example, hardware and software limitations may limit a DAS sampling rate to 1408 Hz. For a 0.5 s scan, 704 views per gantry rotation would be obtained in such a system, a 28.5% reduction compared to systems providing 984 views per gantry rotation. If proper compensation is not performed, view aliasing artifacts, such as streaks, will result. Such aliasing artifacts are known to be quite objectionable to radiologists.

Because the artifacts result from reduction of view sampling, it would seem logical to try to increase a number of views in a reconstruction with interpolation in a view direction. For example, a 2:1 view expansion of an acquired data set could be attempted to increase a number of acquired views from 704 to 1408. This approach, however, leads to a significant reduction in spatial resolution, because view interpolation is typically a low-pass filtering process. Phantom experiments indicate that the degradation in spatial resolution can reach clinically unacceptable levels.

It would therefore be desirable to provide methods and apparatus for CT imaging with reduction of view aliasing artifacts without clinically unacceptable reduction in spatial resolution.

In many clinical scans, projection weighting prior to image reconstruction is necessary. For example, halfscan weighting has been implemented to shorten scan time by approximately 40%. Underscan weighting is used to suppress patient motion in axial scan protocols. On the other hand, helical weightings ("High Quality" or HQ mode, and "High Speed" or HS mode, for example) have been used to avoid artifacts resulting from constant table translation during a scan. It would therefore be desirable to provide methods and apparatus for CT imaging that provide reduced view aliasing artifacts for cases in which projection weighting prior to image reconstruction is necessary. It would also be desirable for such methods and apparatus to operate without requiring the use of conjugate samples, so that halfscan reconstruction is possible.

BRIEF SUMMARY OF THE INVENTION

In one embodiment, the present invention is a method for computerized tomographic (CT) imaging of an object. The method includes steps of scanning an object with a CT imaging system to acquire views that include projection samples of an object; interpolating the acquired views within a selected view range to produce interpolated views; weighting the interpolated views to compensate for the interpolation; weighting the acquired views; and filtering and back-projecting the weighted, interpolated views and the weighted acquired views to generate an image of the object.

Improved CT imaging is provided in this embodiment by reducing view aliasing artifacts without requiring the use of conjugate samples.

DETAILED DESCRIPTION OF THE INVENTION

Figure 1:
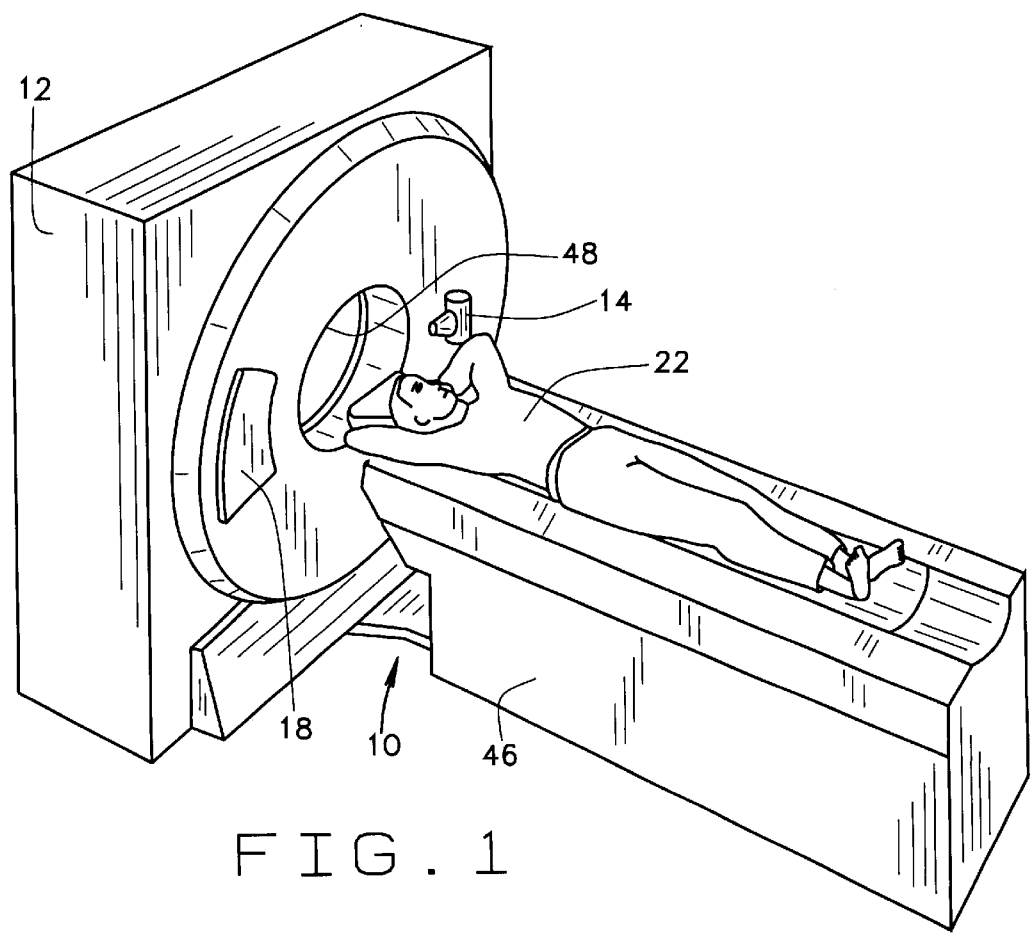
FIG. 1 is a pictorial view of a CT imaging system.
Figure 2:
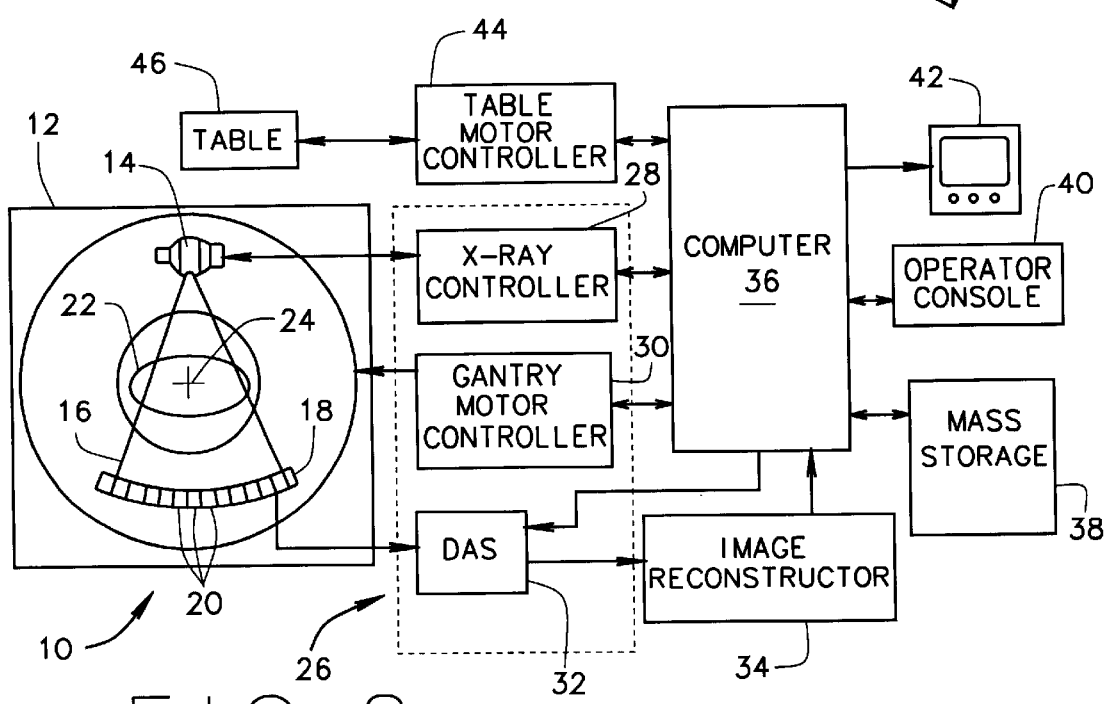
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS)

32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

A majority of clinical aliasing artifacts occur when a dense object is located near an outer region of a field of view, because the view requirement is roughly proportional to the distance of an object from the CT isocenter. In human anatomy, dense objects causing aliasing are predominantly oriented in a horizontal direction. For example, shoulder bones 50 of patient 22, which are typically oriented horizontally when patient 22 is scanned, often produce aliasing streaks. It is desirable to provide a maximum of aliasing reduction in a direction in which aliasing occurs most often, and a minimum of aliasing reduction in a direction in which aliasing occurs less frequently. Such an aliasing reduction configuration provides a good compromise between aliasing artifact reduction and reduction of spatial resolution.

Thus, in one embodiment of the present invention, an object 22, for example, a patient, is scanned with CT imaging system 10 to acquire views comprising projection samples of the object 22. These views are further processed by image reconstructor 34 into images that are stored by computer 36 in storage device 38 for viewing on CRT display 42. (Because design choices are available in which distributed processing of images in various CT imaging systems 10 is performed, it will be understood that the invention is not limited to embodiments in which all processing is performed by a discrete image reconstructor 34.) This processing, in one embodiment, includes steps interpolating acquired views of the object within a selected view range to produce interpolated views; weighting the views, including weighting the interpolated views to compensate for the interpolation and weighting the acquired views; and filtering and backprojecting the weighted interpolated views and the weighted views to generate an image of the object. For a selected view range, the interpolation is uniform. For the range of (0, 2π), the interpolation is nonuniform. In one embodiment, an additional scan-dependent weighting (for example, half scan, underscan, or helical) is applied by CT imaging system 10 so that the acquired views already have a scan-type dependent weighting.

View interpolation of the acquired views is carried out in a view range of $[0.5\pi-\beta_0-\beta_1, 0.5\pi+\beta_0+\beta_1]$ and $[1.5\pi-\beta_0-\beta_1, 1.5\pi+\beta_0+\beta_1]$, where $\beta_0$ and $\beta_1$ are parameters. In one embodiment, parameters $\beta_0$ and $\beta_1$ are both equal to 0.357 radians (20.45°) and are modifiable during clinical stages. Many view interpolation schemes are suitable. For example, a general Lagrange interpolation is used in one embodiment. A set of projection samples $p(\gamma,\beta_i)$ of the views of object 22 is located at view angles $\beta_i$, where $\gamma$ is a projection fan angle, i=1, ..., N and N is the number of views used for interpolation. (In one embodiment, the set of projection samples $p(\gamma,\beta_i)$ is weighted. For example, half scan, underscan, or helical weighting is used.) An estimated projection $p'(\gamma,\beta)$ at location $\beta$ is written as:

$$p'(\gamma, \beta) = \sum_{i=1}^{N} \xi_i p(\gamma, \beta_i), \qquad (2)$$

where:

$$\xi_i = \frac{\prod_{\forall k \neq i}(\beta - \beta_k)}{\prod_{\forall k \neq i}(\beta_i - \beta_k)}. \qquad (2)$$

A Lagrange interpolator, for example, a fourth-order Lagrange interpolator used in one embodiment, advantageously preserves original acquired data samples when $\beta=\beta_i$. To avoid streak artifacts resulting from sharp transitions near boundaries of an interpolation range, interpolated views are weighted prior to the filtered backprojection process by a function $w(\gamma,\beta)$ written as:

$$w(\gamma, \beta) = \begin{cases} \alpha(3\theta^2 - 2\theta^3) & \beta_c - \beta_0 - \beta_1 \leq \beta < \beta_c - \beta_0 \\ \alpha & \beta_c - \beta_0 \leq \beta \leq \beta_c + \beta_0 \\ \alpha - \alpha(3\psi^2 - 2\psi^3) & \beta_c + \beta_0 < \beta < \beta_c + \beta_0 + \beta_1 \end{cases} \qquad (3)$$

where $\beta_c=0.5\pi$ or $\beta_c=1.5\pi$, and is dependent on the interpolated projection region;

$\alpha$ is a parameter, which in one embodiment, is equal to 0.25;

$$\left. \begin{array}{l} \theta = \dfrac{\beta - (\beta_c - \beta_0 - \beta_1)}{\beta_1}; \text{ and} \\ \psi = \dfrac{\beta - (\beta_c + \beta_0)}{\beta_1}. \end{array} \right\} \qquad (4)$$

Because projection samples are not interpolated uniformly across a range of 2π, the ray sampling pattern is no longer homogeneous. More specifically, for each ray path, a sampling density is increased in regions in which interpolation takes place. Therefore, proper compensation is provided to reduce shading artifacts.

In one embodiment, the method does not rely on conjugate samples. If conjugate samples had to be used for non-uniform sampling, the smallest data set to reconstruct an image is a set of projections spanning 2π projection angle. (The projection angle for the sample $(\gamma,\beta)$ is $\beta+\pi-2\gamma$.) A minimum data set for fan beam reconstruction covers an angular range of $\pi+2\gamma_m$, where $\gamma_m$ is a maximum fan angle. A data set that contains the conjugate samples of the minimum data set, plus the minimum data set itself, spans a projection angle of 2π or larger. Therefore, methods that rely upon conjugate samples cannot be used for halfscan reconstructions (using $\pi+2\gamma_m$ projection angles). Embodiments of the present method rely upon locally preserving contributions to a reconstructed image, i.e., the total contribution of the original acquired views and the interpolated views at any β neighborhood is kept constant.

The overall contribution from all samples is kept constant by providing proper weights to samples of the original acquired views. More specifically, the contribution of original or weighted acquired samples are reduced by a same amount to ensure that overall homogeneity is preserved.

In one embodiment, acquired views are weighted by a weighting function $w'(\gamma,\beta)$ prior to the filtered backprojection. For ease of reference, let Γ denote a region in which w'(γ,β) is applied. Outside Γ, w'(γ,β)=1. Otherwise, w'(γ,β) is written:

$$w'(\gamma, \beta) = \begin{cases} 1 - \alpha(3\theta'^2 - 2\theta'^3) & \beta_c - \beta_0 - \beta_1 \le \beta < \beta_c - \beta_0 \\ 1 - \alpha & \beta_c - \beta_0 \le \beta < \beta_c + \beta_0 \\ 1 - \alpha + \alpha(3\psi'^2 - 2\psi'^3) & \beta_c + \beta_0 < \beta \le \beta_c + \beta_0 + \beta_1 \end{cases} \quad (5)$$

where $\beta_c=0.5\pi$ or $\beta_c=1.5\pi$, depending upon an interpolated projection region, $$\left. \begin{aligned} \theta' &= \frac{\beta - (\beta_c - \beta_0 - \beta_1)}{\beta_1}; \text{ and} \\ \psi' &= \frac{\beta - (\beta_c + \beta_0)}{\beta_1}. \end{aligned} \right\} \quad (6)$$

For many clinical applications, additional weighting functions are applied to the acquired views to compensate for projection data inconsistency. For example, to compensate for patient motion, an under-scan weight is applied. For helical applications, helical-related weighting functions are applied to reduce helical artifacts. Thus, in one embodiment, the adaptive interpolation described above is used in conjunction with at least one other scan type-dependent weighting function. The interpolated views are obtained based on the scan type dependent weighted, acquired data, rather than the original acquired data. Thus, the processing of equations (1)–(6) is applied to the scan type dependent weighted projections. The weighted, acquired views (which are weighted both by the scan type dependent weighting and by w'(γ,β)) and the weighted, interpolated views are filtered and backprojected to formulate an image of the object.

It will thus be appreciated that embodiments of the present invention utilize an interpolation that is suitable for all scan type dependent weightings. A further advantage is that embodiments of the present invention do not rely upon conjugate samples for compensation.

Using an embodiment of the present invention in which scan type dependent weighting occurs prior to adaptive interpolation, an exemplary image of a phantom was reconstructed from data acquired using 0.5 s helical scan at 3:1 pitch (corresponding to an HQ mode). This image exhibited an image quality comparable to that of a 0.8 s helical scan in which only helical weights were applied prior to reconstruction.

From the preceding description of various embodiments of the present invention, it is evident that methods and apparatus of the present invention provide improved CT imaging by reducing view aliasing artifacts without simultaneously reducing spatial resolution to clinically unacceptable levels. Where weighting prior to image reconstruction is necessary, embodiments of the present invention in which adaptive interpolation is applied after weighting provide improved image quality, even when conjugate samples are not available.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for computerized tomographic (CT) imaging of an object, said method comprising:

scanning an object with a CT imaging system to acquire views comprising projection samples of an object;

interpolating the acquired views within a selected view range to produce interpolated views;

weighting the interpolated views to compensate for the interpolation;

weighting the acquired views; and filtering and backprojecting the weighted, interpolated views and the weighted acquired views to generate an image of the object.

2. A method in accordance with claim 1 wherein scanning an object with a CT imaging system to acquire views comprising projection samples of an object comprises the step of applying a weighting dependent upon a type of scan performed to produce the acquired views.

3. A method in accordance with claim 1 wherein interpolating the acquired views within a selected range comprises the step of interpolating the acquired views within a view range of $[0.5\pi-\beta_0-\beta_1, 0.5\pi+\beta_0+\beta_1]$ or $[1.5\pi-\beta_0-\beta_1, 1.5\pi+\beta_0+\beta_1]$, where $\beta_0$ and $\beta_1$ are parameters.

4. A method in accordance with claim 3 wherein $\beta_0=\beta_1=0.357$ radians.

5. A method in accordance with claim 3 wherein the object is a patient and further comprising the step of modifying parameters $\beta_0$ and $\beta_1$ during a clinical stage of the patient.

6. A method in accordance with claim 3 wherein interpolating acquired views within a selected view range comprises the step of applying a Lagrange interpolator to acquired projection samples of the views of the object.

7. A method in accordance with claim 6 wherein applying a Lagrange interpolator to the acquired projection samples of the views of the object comprises the step of applying a fourth-order Lagrange interpolator to the acquired projection samples of the views of the object.

8. A method in accordance with claim 6 wherein applying a Lagrange interpolator to the acquired projection samples of the views of the object comprises the step of determining an estimated projection p'(γ,β) at a location β, where p'(γ,β) is written as:

$$p'(\gamma, \beta) = \sum_{i=1}^{N} \xi_i p(\gamma, \beta_i),$$

where:

$$\xi_i = \frac{\prod_{\forall k \ne i} (\beta - \beta_k)}{\prod_{\forall k \ne i} (\beta_i - \beta_k)};$$

$p(\gamma,\beta_i)$ is a set of projection samples located at a view angle $\beta_i$, where i=1, . . . ,N, and N is a number of views for interpolation; and γ is a projection fan angle.

9. A method in accordance with claim 8 wherein weighting the interpolated views comprises the step of weighting the interpolated views with a function written as:

$$w(\gamma, \beta) = \begin{cases} \alpha(3\theta^2 - 2\theta^3) & \beta_c - \beta_0 - \beta_1 \le \beta < \beta_c - \beta_0 \\ \alpha & \beta_c - \beta_0 \le \beta \le \beta_c + \beta_0 \\ \alpha - \alpha(3\psi^2 - 2\psi^3) & \beta_c + \beta_0 < \beta < \beta_c + \beta_0 + \beta_1 \end{cases}$$

where $\beta_c = 0.5\pi$ or $\beta_c = 1.5\pi$, dependent on a region of the interpolated projection samples;

$\alpha$ is a parameter, $$\theta = \frac{\beta - (\beta_c - \beta_0 - \beta_1)}{\beta_1}, \text{ and } \psi = \frac{\beta - (\beta_c + \beta_0)}{\beta_1}.$$

10. A method in accordance with claim 9 wherein $\alpha = 0.25$.

11. A method in accordance with claim 3 wherein weighting the acquired views comprises the step of weighting the acquired views with a function w'($\gamma,\beta$) written as:

$$w'(\gamma, \beta) = \begin{cases} 1 - \alpha(3\theta'^2 - 2\theta'^3) & \beta_c - \beta_0 - \beta_1 \le \beta < \beta_c - \beta_0 \\ 1 - \alpha & \beta_c - \beta_0 \le \beta < \beta_c + \beta_0 \\ 1 - \alpha + \alpha(3\psi'^2 - 2\psi'^3) & \beta_c + \beta_0 < \beta \le \beta_c + \beta_0 + \beta_1 \end{cases}$$

where $\beta_c = 0.5\pi$ or $\beta_c = 1.5\pi$, depending upon an interpolated projection region, $$\theta' = \frac{\beta - (\beta_c - \beta_0 - \beta_1)}{\beta_1}; \quad \psi' = \frac{\beta - (\beta_c + \beta_0)}{\beta_1};$$

and $\alpha$ is a parameter.

12. A computerized tomographic (CT) imaging system for producing an image of an object, said system configured to:
   scan an object to acquire views comprising projection samples of an object;
   interpolate the acquired views within a selected view range to produce interpolated views;
   weight the interpolated views to compensate for the interpolation;
   weight the acquired views; and
   filter and backproject the weighted, interpolated views and the weighted acquired views to generate an image of the object.

13. A system in accordance with claim 12 wherein said system being configured to scan an object to acquire views comprising projection samples of an object comprises said system being configured to apply a weighting dependent upon a type of scan performed to produce the acquired views.

14. A system in accordance with claim 12 wherein said system being configured to interpolate the acquired views within a selected range comprises said system being configured to interpolate the acquired views within a view range of [$0.5\pi-\beta_0-\beta_1, 0.5\pi+\beta_0+\beta_1$] or [$1.5\pi-\beta_0-\beta_1, 1.5\pi+\beta_0+\beta_1$], where $\beta_0$ and $\beta_1$ are parameters.

15. A system in accordance with claim 14 wherein $\beta_0 = \beta_1 = 0.357$ radians.

16. A system in accordance with claim 14 firther configured to modify parameters $\beta_0$ and $\beta_1$ during a clinical stage of the patient.

17. A system in accordance with claim 14 wherein said system being configured to interpolate acquired views within a selected view range comprises said system being configured to apply a Lagrange interpolator to acquired projection samples of the views of the object.

18. A system in accordance with claim 17 wherein said system being configured to apply a Lagrange interpolator to the acquired projection samples of the views of the object comprises said system being configured to apply a fourth-order Lagrange interpolator to the acquired projection samples of the views of the object.

19. A system in accordance with claim 17 wherein said system being configured to apply a Lagrange interpolator to the acquired projection samples of the views of the object comprises said system being configured to determine an estimated projection p'($\gamma,\beta$) at a location $\beta$, where p'($\gamma,\beta$) is written as:

$$p'(\gamma, \beta) = \sum_{i=1}^{N} \xi_i p(\gamma, \beta_i),$$

$$\text{where: } \xi_i = \frac{\prod_{\forall k \ne i} (\beta - \beta_k)}{\prod_{\forall k \ne i} (\beta_i - \beta_k)};$$

p($\gamma,\beta_i$) is a set of projection samples located at a view angle $\beta_i$, where i=1, . . . ,N, and N is a number of views for interpolation; and $\gamma$ is a projection fan angle.

20. A system in accordance with claim 19 wherein said system being configured to weight the interpolated views comprises said system being configured to weight the interpolated views with a function written as:

$$w(\gamma, \beta) = \begin{cases} \alpha(3\theta^2 - 2\theta^3) & \beta_c - \beta_0 - \beta_1 \le \beta < \beta_c - \beta_0 \\ \alpha & \beta_c - \beta_0 \le \beta \le \beta_c + \beta_0 \\ \alpha - \alpha(3\psi^2 - 2\psi^3) & \beta_c + \beta_0 < \beta < \beta_c + \beta_0 + \beta_1 \end{cases}$$

where $\beta_c = 0.5\pi$ or $\beta_c = 1.5\pi$, dependent on a region of the interpolated projection samples;

$\alpha$ is a parameter, $$\theta = \frac{\beta - (\beta_c - \beta_0 - \beta_1)}{\beta_1}, \text{ and } \psi = \frac{\beta - (\beta_c + \beta_0)}{\beta_1}.$$

21. A system in accordance with claim 20 wherein $\alpha = 0.25$.

22. A system in accordance with claim 14 wherein said system being configured to weight the acquired views comprises said system being configured to weight the acquired views with a function w'($\gamma,\beta$) written as:

$$w'(\gamma, \beta) = \begin{cases} 1 - \alpha(3\theta'^2 - 2\theta'^3) & \beta_c - \beta_0 - \beta_1 \le \beta < \beta_c - \beta_0 \\ 1 - \alpha & \beta_c - \beta_0 \le \beta < \beta_c + \beta_0 \\ 1 - \alpha + \alpha(3\psi'^2 - 2\psi'^3) & \beta_c + \beta_0 < \beta \le \beta_c + \beta_0 + \beta_1 \end{cases}$$

where $\beta_c = 0.5\pi$ or $\beta_c = 1.5\pi$, depending upon an interpolated projection region, $$\theta' = \frac{\beta - (\beta_c - \beta_0 - \beta_1)}{\beta_1}; \quad \psi' = \frac{\beta - (\beta_c + \beta_0)}{\beta_1};$$

and $\alpha$ is a parameter.

* * * * *

UNITED STATES PATENT AND TRADEMARK OFFICE
CERTIFICATE OF CORRECTION

PATENT NO.    : 6,327,325 B1
DATED         : December 4, 2001
INVENTOR(S)   : Jiang Hsieh It is certified that error appears in the above-identified patent and that said Letters Patent is hereby corrected as shown below:

<u>Column 7,</u>
Line 20, after "w'($\gamma$,$\beta$)" insert an equal sign -- = --.
Line 60, delete "firther" and insert therefor -- further --.

<u>Column 8,</u>
Line 34, after "w($\gamma$,$\beta$)" insert an equal sign -- = --.
Line 54, after "w'($\gamma$,$\beta$)" insert an equal sign -- = --.
Line 58, after "$\beta_c={}^{1.5}\pi$" and insert therefor -- $\beta_c=1.5\pi$ --.

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,327,325 B1
DATED : December 4, 2001
INVENTOR(S) : Jiang Hsieh

It is certified that error appears in the above-identified patent and that said Letters Patent is hereby corrected as shown below:

Column 8,
Line 58, delete "$\beta_c=^{1.5}\pi$" and insert therefor -- $\beta_c=1.5\pi$ --.

Signed and Sealed this

Eighth Day of June, 2004

JON W. DUDAS
*Acting Director of the United States Patent and Trademark Office*